US009585602B1

(12) United States Patent
Navarro et al.

(10) Patent No.: US 9,585,602 B1
(45) Date of Patent: Mar. 7, 2017

(54) OBTAINING MEDICAL DIAGNOSTIC MEASUREMENTS

(71) Applicant: Intellirod Spine Inc., Akron, OH (US)

(72) Inventors: Richard R. Navarro, Hinckley, OH (US); Steven E. Wilder, Ashland, OH (US)

(73) Assignee: Intellirod Spine Inc., Adron, OH (US)

( * ) Notice: Subject to any disclaimer, the term of this patent is extended or adjusted under 35 U.S.C. 154(b) by 86 days.

(21) Appl. No.: 14/508,506

(22) Filed: Oct. 7, 2014

Related U.S. Application Data

(60) Provisional application No. 61/887,644, filed on Oct. 7, 2013.

(51) Int. Cl.
| | |
|---|---|
| *A61B 5/103* | (2006.01) |
| *A61B 5/117* | (2016.01) |
| *A61B 5/107* | (2006.01) |
| *A61B 5/00* | (2006.01) |
| *A61B 5/11* | (2006.01) |

(52) U.S. Cl.
CPC .......... *A61B 5/1071* (2013.01); *A61B 5/6801* (2013.01); *A61B 5/742* (2013.01); *A61B 5/7405* (2013.01); *A61B 5/0031* (2013.01); *A61B 5/11* (2013.01); *A61B 5/1116* (2013.01); *A61B 5/4528* (2013.01); *A61B 5/684* (2013.01); *A61B 5/6843* (2013.01); *A61B 5/6844* (2013.01); *A61B 5/7221* (2013.01); *A61B 2562/0219* (2013.01)

(58) Field of Classification Search
CPC ....... A61B 5/0031; A61B 5/1071; A61B 5/11; A61B 5/6801; A61B 5/684; A61B 5/6843; A61B 5/6844; A61B 5/7405; A61B 5/742; A61B 2562/0219; A61B 5/1116; A61B 5/7221; A61B 5/4528

See application file for complete search history.

(56) References Cited

U.S. PATENT DOCUMENTS

| | | | |
|---|---|---|---|
| 5,179,942 A | 1/1993 | Drulias et al. | |
| 6,083,248 A | 7/2000 | Thompson | |
| 6,341,504 B1 | 1/2002 | Istook | |
| 7,632,216 B2 | 12/2009 | Rahman et al. | |
| 8,016,776 B2 * | 9/2011 | Bourget | A61B 5/0002 600/382 |
| 8,073,548 B2 | 12/2011 | Colvin, Jr. et al. | |
| 9,241,673 B2 * | 1/2016 | Sabesan | A61B 5/0245 |
| 2009/0209830 A1 * | 8/2009 | Nagle | A43B 7/147 600/301 |
| 2009/0275867 A1 | 11/2009 | Santos-Manne et al. | |
| 2011/0125063 A1 | 5/2011 | Shalon et al. | |
| 2011/0195666 A1 | 8/2011 | Forsell | |
| 2011/0201969 A1 * | 8/2011 | Hatlestad | A61B 5/1116 600/587 |
| 2012/0071793 A1 | 3/2012 | Gal et al. | |
| 2012/0123232 A1 | 5/2012 | Najarian et al. | |
| 2012/0184826 A1 | 7/2012 | Keenan et al. | |
| 2013/0030711 A1 * | 1/2013 | Korhonen | G06K 9/0051 702/19 |
| 2013/0079693 A1 | 3/2013 | Ranky et al. | |

(Continued)

*Primary Examiner* — Devin Henson
(74) *Attorney, Agent, or Firm* — Middleton Reutlinger; Robert H. Eichenberger; Brantley C. Shumaker

(57) ABSTRACT

Systems, methods, computer-readable media (e.g., transitory and non-transitory) and apparatus are described herein for obtaining medical diagnostic measurements that are accurate and/or consistent over time.

10 Claims, 5 Drawing Sheets

(56) References Cited

U.S. PATENT DOCUMENTS

2013/0237865 A1\* 9/2013 Sato ................... A61B 5/02233
              600/499
2014/0046403 A1 2/2014 Aghassian
2014/0062717 A1 3/2014 Mudumbai et al.
2014/0066814 A1 3/2014 Gupta et al.

\* cited by examiner

OBTAINING MEDICAL DIAGNOSTIC MEASUREMENTS

BACKGROUND

Obtaining medical diagnostic measurements that are accurate and/or consistent over time may be difficult. For example, at a first appointment where an X-ray is taken of a patient's body segment (e.g., arm, leg, back, etc.), e.g., after lumbar fusion surgery to determine if fusion has been achieved, the body segment may be aligned in a particular manner, e.g., relative to other body segments. Various internal structures such as bones, cartilage, tendons, organs, and so forth may be in a particular alignment relative to one another. At a subsequent appointment where a similar X-ray is taken, it may be difficult to recreate the particular configuration of internal structures and loads on those structures present when the first X-ray or X-rays was/were taken. This may lead medical personnel to draw inaccurate conclusions from the measured data. For example, a difference in data between the two X-rays may be attributable to the difference in body segment configuration, rather than a physiological change in the patient.

As another example, implanted sensors may measure, and make available to other devices using wireless technology, strain readings, e.g., from body segments or joints in between. The strain measured by such sensors may depend in large part on an angle/orientation of two body segments relative to one another. If readings are taken from such sensors on two different visits, and the patient is not oriented or aligned the same during those visits, the measurements taken from the implanted sensors may be skewed or otherwise unreflective of actual physiological change.

For example, on one visit, a spinal fusion patient may take two (or more) X-rays and strain measurements: a first X-ray and strain measurement while the patient is bent at a first angle; and a second X-ray and strain measurement while the patient is bent at a second angle. A delta strain may be recorded between the two strain measurements. At a subsequent visit, X-rays and strain measurements may need to be taken at the same two angles.

While mechanical devices exist to facilitate consistent body segment alignment—and hence, consistent measurements over time—these devices tend to be expensive, cumbersome and/or may yield inconsistent results.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Figure 1:
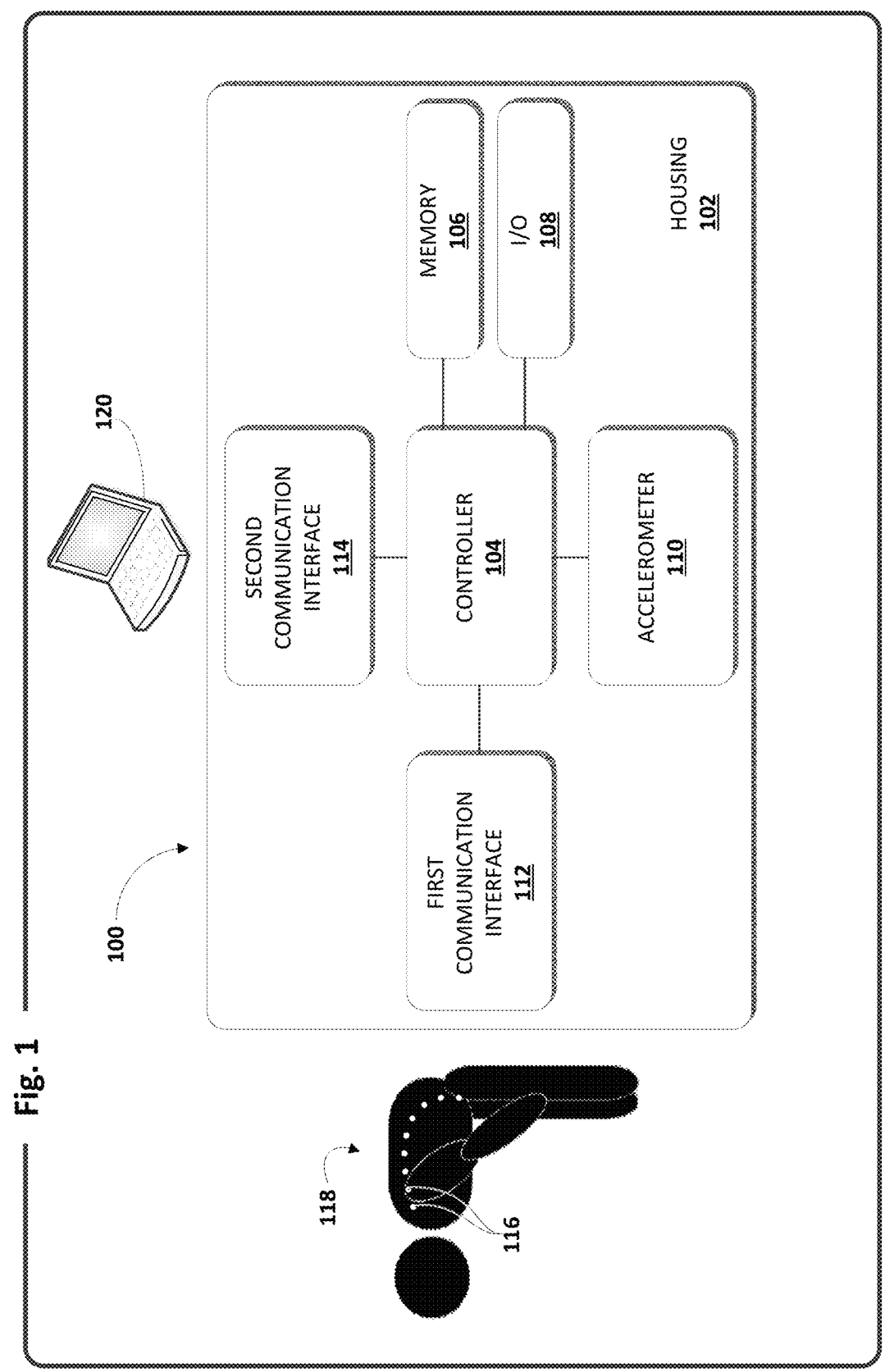
FIG. 1 schematically illustrates example components of an electronic orientation-measurement device, in accordance with various embodiments.

Referring to FIG. 1, in one embodiment, an electronic orientation-measurement device 100 may include a housing 102. Electronic orientation-measurement device 100 may include various components inside of housing 102, such as a controller 104. In various embodiments, controller 104 may include one or more computer processors, sometimes referred to as "microprocessors," that may be configured (e.g., by executing instructions) to perform various functions. In some embodiments, low cost, 8-bit microprocessors may be employed. In some embodiments, controller 104 may be partially or wholly-hardware controlled, and may include, for instance, one or more application-specific integrated circuits (ASICs).

In various embodiments, housing 102 may be constructed out of various materials and may have various shapes. In some embodiments, housing 102 may be relatively flat, and may be constructed out of a semi-flexible material such as leather, nylon, or other similar textiles or materials. In some embodiments, housing 102 may be further shaped like a paddle, with handle that medical personnel may grasp while pressing the paddle against a body segment of a patient.

In various embodiments, controller 104 may be operably coupled with memory 106. Memory 106 may come in various forms, solid state and otherwise, including but not limited to various types of random-access memory (RAM), flash memory, and so forth. Controller 104 may also be operably coupled with one or more input/output ("I/O") devices 108. I/O devices 108 may include various input devices, such as buttons, knobs, capacitive touch pads, piezoelectric elements, and so forth. In some embodiments, I/O devices 108 may include a position switch operable to adjust a desired orientation of a body segment and/or a joint between body segments. In some embodiments, such a position switch may be toggled between a first position for flexion and another position for extension. In other embodiments, separate switches may be provided to control flexion and extension desired orientations. I/O devices 108 may also include various output devices, such as an LCD display, a digital display, one or more speakers, a bank of LED indicators, and so forth.

In various embodiments, electronic orientation-measurement device 100 may include one or more sensors to detect an orientation, or "tilt," of housing 102 relative to a reference vector or angle. For instance, in FIG. 1, electronic orientation-measurement device 100 includes an accelerometer 110 configured to measure an orientation of housing 102 relative to a reference vector or angle representing gravity, and provide data and/or a signal indicative of that measurement, e.g., to controller 104. In various embodiments, accelerometer 110 may include a 1-, 2- and/or -3 axis accelerometer. In other embodiments, in addition to or instead of accelerometer 110, electronic orientation-measurement device 100 may include other components to detect orientation, such as one or more gyroscopes and/or tilt sensors. Although not depicted in FIG. 1, in some embodiments, electronic orientation-measurement device 100 may include other sensors, including but not limited to a thermometer, barometer, Geiger counter, GPS, electrometer, PH meter, and so forth.

In various embodiments, electronic orientation-measurement device 100 may also include, coupled with controller 104, various communication interfaces. For example, in FIG. 1, electronic orientation-measurement device 100 may include a first communication interface 112 and a second communication interface 114. In various embodiments, these interfaces may employ various wired and/or wireless communication technologies to enable controller 104 to exchange data with one or more remote devices.

For instance, first communication interface 112 may establish an inductive link (e.g., 13.56 MHz) with one or more sensors 116 implanted in or secured on a patient's 118 body. Controller 104 may then transmit and receive data through first communication interface 112 to obtain various medical diagnostic measurements from those sensors. Various other types of wireless technology may be employed by first communication interface 112 depending on the technology employed by sensors implanted in or secured on the patient. For example, in some embodiments, near-field communications (NFC), radio-frequency identification (RFID), or other low-power wireless communication technologies may be used. Example sensors that may be implanted in or secured on a patient's body, and with which electronic orientation-measurement device 100 may communicate using first communication interface 112, include but are not limited to sensors that measure stress loads on joints, e.g., for testing newly grown engineered cartilage or bone between two or more a vertebra or joint, as well as sensors that measure strain in implanted objects such as spinal fusion rods.

Second communication interface 114 may employ the same or a different type of wired or wireless communication technology to communicate with, for instance, one or more remote computing devices 120. For instance, controller 104 may communicate with a laptop computer, tablet, or smart phone operated by a physician using second communication interface 114. Using this interface, controller 104 may provide data, e.g., measured by accelerometer 110, to one or more remote computing devices 120. Medical personnel may save the data, e.g., to a database, and/or manipulate it to make various presentations to the patient or to aid in diagnosis. Various types of wired or wireless technology may be employed by second communication interface 114 depending on the technology employed by one or more remote computing devices 120. For example, in some embodiments, and similar to first communication interface 112, NFC, RFID, or other low-power wireless communication technologies may be used. In other embodiments, Ethernet, Bluetooth, WiFi, WiFi Direct, Serial, USB, and so forth, may be employed.

Figure 2:
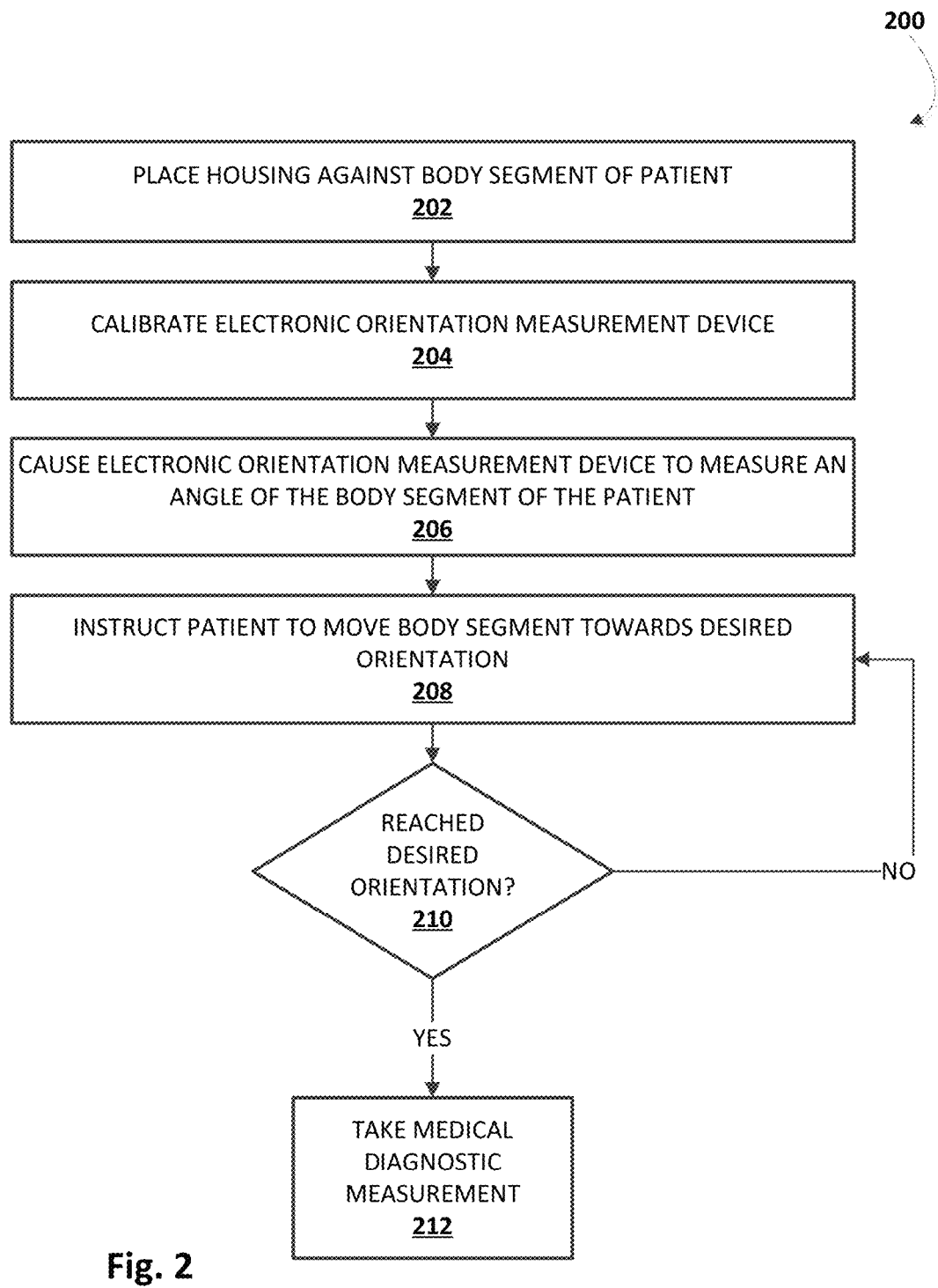
FIG. 2 schematically depicts an example method of using an electronic orientation-measurement device to obtain medical diagnostic measurements that are accurate and/or consistent over time, in accordance with various embodiments.

FIG. 2 depicts an example method 200 that may be practiced to obtain medical diagnostic measurements that are accurate and/or consistent over time, using a device such as electronic orientation-measurement device 100, in accordance with various embodiments. One or more operations of FIG. 2 may be performed variously by medical personnel and/or electronic orientation-measurement device 100, e.g., by way of controller 104 executing a routine stored in memory 106.

At block 202, medical personnel such as a doctor or nurse may place housing 102 of electronic orientation-measurement device 100 against a body segment of a patient, such as the patent's back. In some embodiments, the medical personnel may simply hold electronic orientation-measurement device 100 against the patient's body segment. In other embodiments, electronic orientation-measurement device 100 may be secured to the patient, e.g., using adhesive and/or straps. In yet other embodiments, electronic orientation-measurement device 100 may be incorporated (e.g., removably or permanently) into or onto a medical device worn by a patient, such as a back brace, a neck brace, a medical boot, a cast, and so forth. At block 204, electronic orientation-measurement device 100 may be calibrated, e.g., by detecting vertical (e.g., the vector corresponding to gravity) and equating it to, for instance, zero degrees. This detected angle may thereafter be a reference angle usable to determine proximity to a desired angle or orientation.

At block 206, the medical professional may cause electronic orientation-measurement device 100 to measure an angle of the patient's body segment, e.g., relative to the reference angle determined at block 204, using accelerometer 110. For example, a doctor may press a button (e.g., I/O device 108) on electronic orientation-measurement device 100 that causes accelerometer 110 to provide output indicative of a current orientation of housing 102 as it is pressed against the patient's back. Thereafter, accelerometer 110 may continuously and/or repeatedly measure the orientation and provide the result to controller 104.

At block 208, the patient may be instructed to move the segment of the patient's body (e.g., via flexion or extension) to be measured towards a certain desired orientation. For example, the patient may be instructed, e.g., by medical personnel or via a display (e.g., I/O device 108) on electronic orientation-measurement device 100, to lean forward or backward until electronic orientation-measurement device 100 provides audible or visual output, e.g., via I/O device 108, to indicate that housing 102 is sufficiently close to the desired orientation. In some embodiments, the desired orientation may be a particular angle at which the patient's body segment should be oriented to obtain the best medical diagnostic measurement. In some embodiments, the desired orientation may be a previously-recorded measured orientation, e.g., stored in memory 106 of electronic orientation-measurement device 100. Using previously-recorded measurements enables medical personnel to take consistent medical diagnostic measurements over time.

For example, suppose that during a first follow-up appointment after lumbar fusion surgery, a delta angle in a patient's sagittal plane is measured between flexion and extension. During the measurement, the patient was bent over to 45 degrees when an X-ray of her spine was taken. At subsequent visits, electronic orientation-measurement device 100 may be used by medical personnel to ensure that the patient is bent over to the same degree, so that a new X-ray is consistent with the previous X-ray. This may more clearly demonstrate physiological changes (e.g., healing, regeneration, deterioration, etc.) that may have occurred in the patient since her last visit, rather than incidental changes in the patient's angle between visits.

At block 210, electronic orientation-measurement device 100 may determine, e.g., by controller 104 repeatedly comparing newly-received output from accelerometer 110 to a desired angle or orientation, whether the segment of the patient's body is properly oriented, e.g., relative to another segment. In some embodiments, controller 104 may determine that the body segment is properly oriented when it is equal to, approximately equal to, and/or within a predetermined range of, the desired angle or orientation. In some embodiments, a body segment may be properly oriented when its measured angle or orientation is sufficiently close to the desired angle or orientation that any changes in a medical diagnostic measurement are most likely attributable to physiological change, rather than disorientation of the body segment(s). If the answer at block 210 is no, then method 200 may proceed back to block 208, However, if the answer at block 210 is yes, then method 200 may proceed to block 212, at which a medical diagnostic measurement may be taken.

In some embodiments, at block 212, the medical professional may take the medical diagnostic measurement manually, e.g., in response to the audible or visual output. For example, the medical professional may wait for an audible tone or visual indicator from electronic orientation-measurement device 100, and may operate an X-ray upon receiving the audible or visual output. In some embodiments, a speaker on electronic orientation-measurement device (e.g., I/O device 108) may provide output in the form of a beep or tone that increases in frequency as housing 102 approaches a desired orientation. In some embodiments, the tone may become virtually constant when housing 102 reaches the desired orientation. In other embodiments, at block 212, the medical diagnostic measurement may be taken automatically, e.g., in response to electronic orientation-measurement device 100 determining that an orientation of the patient's body segment is sufficiently close to a desired orientation.

In some embodiments, electronic orientation-measurement device 100 itself may take the measurement, e.g., by communicating with a sensor 116 implanted in or secured on the patient's body using first communication interface 112 to obtain the medical diagnostic measurement. In other embodiments, electronic orientation-measurement device 100 may cause another device to take the measurement. For example, electronic orientation-measurement device 100 may transmit a signal, e.g., over second communication interface 114 to one or more remote computing devices 120, to cause the remote computing devices 120 to cause the medical diagnostic measurement to be taken. For instance, one or more remote computing devices 120 may control an X-ray machine, and may automatically cause the X-ray machine to take an X-ray in response to receipt of a signal from electronic orientation-measurement device 100 that the patient has oriented the portion of her body to be sufficiently close to the desired orientation.

Figure 3:
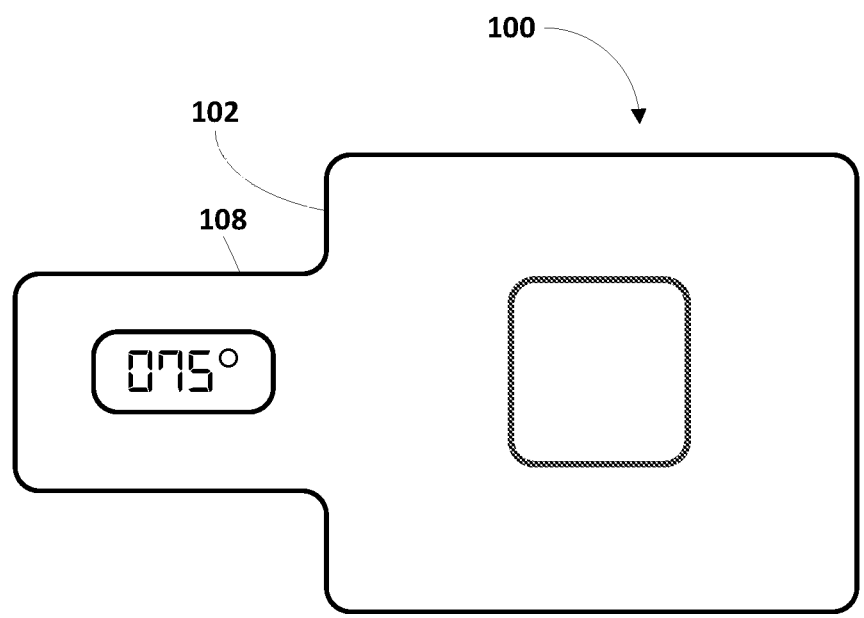
FIG. 3 is a view of an example electronic orientation-measurement device, in accordance with various embodiments.

FIGS. 3A and B depict FIG. 3 depicts an example electronic orientation-measurement device 100, in accordance with various embodiments. In this example, electronic orientation-measurement device 100 has a housing 102 that is shaped like a paddle. Housing 102 may be constructed using a flexible material, such as rubber or leather. An I/O device 108 is provided in the form of an LCD display, which controller 104 (not shown in FIG. 3) may cause to render the current orientation of housing 102 (75 degrees is shown).

As noted above, the electronic orientation-measurement device 100 shown in FIG. 3 may be placed against a patient's back when standing, and medical personnel may actuate it (e.g., by pressing a button). In some embodiments electronic orientation-measurement device 100 may at that point be calibrated. Then, medical personnel may instruct the patient to lean forward until I/O device 108 reads the desired angle. At that point, based on the output on the LCD display or in response to an audible or other output, medical personnel may instruct the patient to hold still. Medical personnel may then take the medical diagnostic measurement. As noted above, in some embodiments, electronic orientation-measurement device 100 itself may automatically initiate the taking of the medical diagnostic measurement, e.g., by communicating with sensors (e.g., 116) implanted in or secured on the patient and/or by causing a remote computing device (e.g., 120) to initiate the medical diagnostic measurement.

Figure 4:
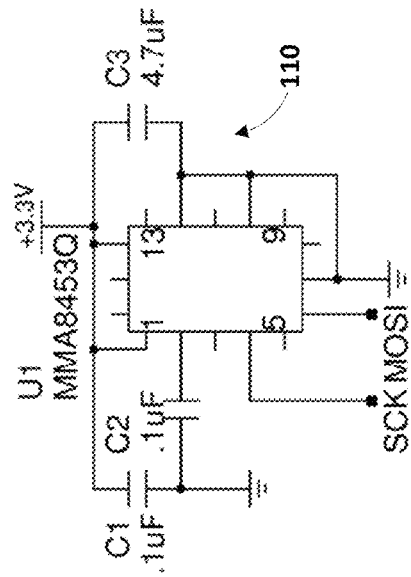
FIG. 4 is a circuit diagram of an example accelerometer, in accordance with various embodiments.

FIG. 4 schematically depicts an example circuit that may be used to implement accelerometer 110, in accordance with various embodiments.

Figure 5:
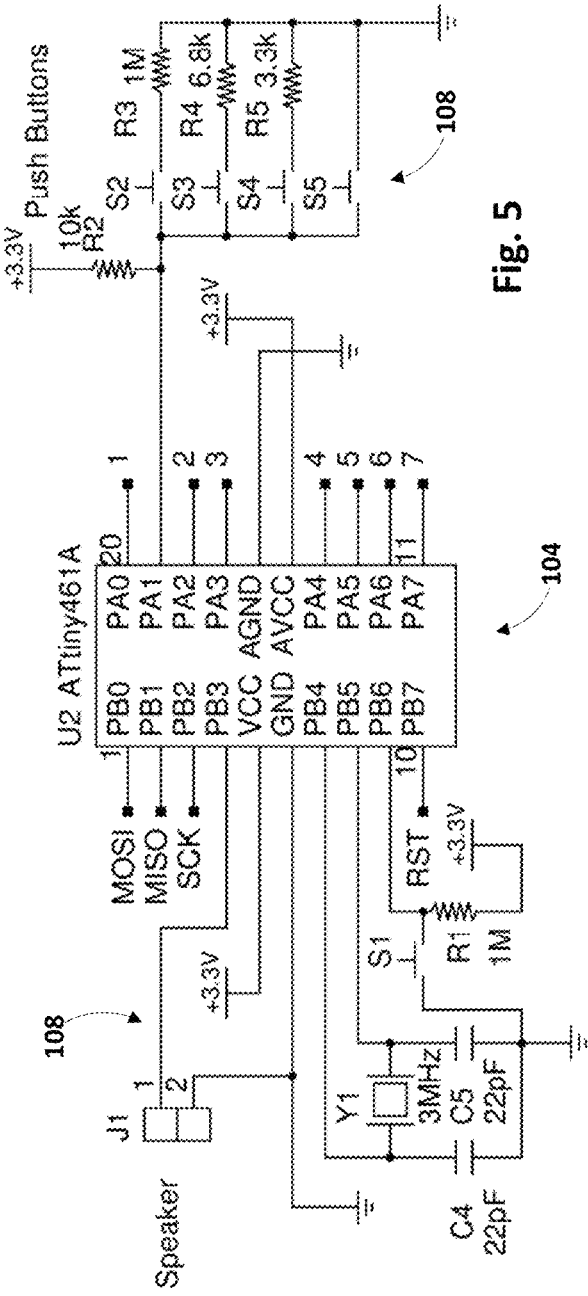
FIG. 5 is a circuit diagram of an example controller operably coupled with various I/O components, in accordance with various embodiments.
Figure 6:
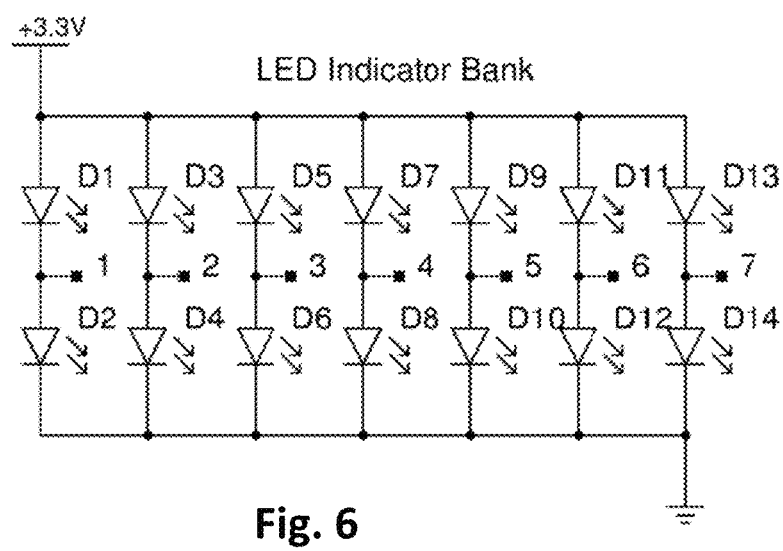
FIG. 6 is a circuit diagram of an example LED indicator bank, in accordance with various embodiments.

FIG. 5 depicts an example circuit that may be used to implement controller 104 and other components. Here, controller 104 is implemented using an ATtiny461A microcontroller by the Atmel Corporation of San Jose, Calif. However, this is not meant to be limiting, and other microcontrollers from Atmel or other manufacturers may be used instead. Controller 104 is operably coupled with various I/O devices 108, including a speaker and push buttons. FIG. 6 depicts a circuit diagram of one example I/O device 108: an LED indicator bank.

In some embodiments, rather than electronic orientation-measurement device 100 being a dedicated device, a portable computing device such as a smart phone or tablet may be used as electronic orientation-measurement device 100. A medical professional's smart phone may be equipped with one or more accelerometers 110, which may be accessible by software executing on the smart phone. The medical professional may download the software (also referred to as an "application," or "app") and install it into computer-readable memory (e.g., memory 106) of her smart phone. When the app is executed by one or more processors of the smart phone, those processors may act as controller 104 described herein, and the smart phone may be used to perform various operations described herein.

For instance, the medical professional may hold the smart phone against a patient's body segment and press a user interface element rendered by the software (e.g., on a touch screen display) to initiate calibration and/or measurement by accelerometer 110. Then, and as described above, the medical professional may instruct the patient to move one or more body segments towards a desired orientation. The smart phone (by way of executing the software) may continuously and/or repeatedly compare the output of accelerometer 110 with a desired orientation/angle, and may raise audio or visual output when the smart phone's orientation is sufficiently close to the desired orientation/angle. In some embodiments, the smart phone may include one or more other components shown in FIG. 1, such as first communication interface 112 and second communication interface 114, and may be able to communication with implanted sensors (116) and other remote computing devices (e.g., 120) as described above. In some cases, the smart phone may be able to further communicate with remote computing devices using various cellular-based communication technologies, which may be referred to as 3G, 4G, 5G, GSM, and so forth.

In some embodiments, electronic orientation-measurement device 100 may be used outside the context of a doctor's office. For example, in some embodiments, electronic orientation-measurement device 100 may be incorporated into a wearable medical apparatus, such as a back or neck brace, a case, and so forth, that a patient wears outside of the doctor's office, either at prescribed times or constantly. In such a scenario, electronic orientation-measurement device 100 may be configured to take medical diagnostic measurements at various times.

In some embodiments, electronic orientation-measurement device 100 may take medical diagnostic measurements in response to the patient reaching some desired state, such as bent over to a desired orientation (e.g., while gardening or exercising). In some embodiments, electronic orientation-measurement device 100 may take medical diagnostic measurements in response to movement of the patient. For example, accelerometer 110 may detect when the patient is moving, e.g., more than a predetermine threshold (e.g., moving more than would be typical when sleeping). On detection of sufficient movement, electronic orientation-measurement device 100 may take one or more medical diagnostic measurements. In some embodiments, electronic orientation-measurement device 100 may take multiple medical diagnostic measurements, e.g., every second or every few milliseconds, for a predetermined time or until the patient stops moving. In various embodiments, electronic orientation-measurement device 100 may store date representing these multiple diagnostic measurements in memory 106 or may transmit the data to a remote computing device (e.g., 120) that may store the data. That data may then be provided to the patient's doctor, e.g., in real time or by the patient at a visit to the doctor's office. For example, the doctor may download medical diagnostic data collected by electronic orientation-measurement device 100 since the last visit, so that the doctor may act accordingly.

While examples described herein have referred primarily to measurements being taken across multiple appointments, this is not meant to be limiting. For example, a patient may be unable to bend early after surgery. In such case, two different spine rod strain loads may be measured at a single appointment in order to determine a delta between them. One load measurement may be collected from an implanted strain sensor when the patient is in a standing, neutral posture. Another load measurement may be collected from the implanted strain sensor while the patient maintains the same posture, but holds weights extended horizontally outward from the shoulder or body. Electronic orientation-measurement device 100 may be used to ensure that the patient is standing at the same angle during both measurements. That way, the determined delta is based wholly on the added weight, and not on a difference in the patient's posture between measurements.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus for obtaining consistent medical diagnostic measurements, comprising:
   a housing that is configured to be secured to or held against a patient;
   memory to store one or more measured orientations of the housing;
   a sensor configured to detect an orientation of the housing; and
   a controller operably coupled to the sensor and the memory and configured to:
   receive, from the sensor, a measured orientation of the housing;
   compare the measured orientation of the housing to a previously measured orientation stored in the memory in association with a previous reading from a strain sensor associated with the patient; and
   provide audible or visible output in response to a determination, based on the comparison, that the measured orientation is within a predetermined range of the previously measured orientation.

2. The apparatus of claim 1, wherein the controller is further configured to record in the memory a measurement received from the strain sensor associated with the patient via a wireless communication interface.

3. The apparatus of claim 2, wherein the controller is further configured to record the measurement automatically in response to the determination, based on the comparison, that the measured orientation is within the predetermined range of the previously measured orientation.

4. The apparatus of claim 1, wherein the sensor is a three-axis accelerometer.

5. The apparatus of claim 1, wherein the controller is activated by a signal generated by the sensor in response to detection of movement by the sensor.

6. The apparatus of claim 1, wherein the controller is further configured to record, in the memory, data indicative of a plurality of measured orientations provided by an accelerometer over a time interval.

7. The apparatus of claim 1, wherein the controller is further configured to provide different audible or visible output to instruct the patient to move a body segment of the patient in response to another determination, based on the comparison, that the measured orientation is not within a predetermined range of the previously measured orientation.

8. The apparatus of claim 7, wherein the different audible or visible output comprises a sound that changes in frequency as the housing approaches the previously measured orientation.

9. The apparatus of claim 1, further comprising an output interface operably coupled with the controller, wherein the audible or visible output is rendered using the output interface.

10. The apparatus of claim 1, wherein the controller is further configured to transmit, to a remote computing device in response to the determination that the measured orientation is within the predetermined range of the previously measured orientation, a signal that causes the remote computing device to operate the strain sensor to take a new reading from the patient.

* * * * *